United States Patent [19]

Fest et al.

[11] 4,248,866
[45] Feb. 3, 1981

[54] COMBATING ARTHROPODS WITH N-(O-ETHYL-S-N-PROPYL-THIOPHOSPHORYLOXY)-NAPHTHALIMIDES

[75] Inventors: Christa Fest; Hellmut Hoffmann, both of Wuppertal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 65,683

[22] Filed: Aug. 10, 1979

[30] Foreign Application Priority Data

Aug. 19, 1978 [DE] Fed. Rep. of Germany ....... 2836328

[51] Int. Cl.³ .................... A01N 57/00; A01N 57/26; C07F 9/06
[52] U.S. Cl. ................................... 424/200; 546/25
[58] Field of Search ........................... 546/25; 424/200

[56] References Cited

U.S. PATENT DOCUMENTS

| | | | |
|---|---|---|---|
| 3,312,706 | 4/1967 | Rigterink | 424/200 |
| 3,484,520 | 12/1969 | DiNetta et al. | 424/200 |
| 3,821,246 | 6/1974 | Kishino et al. | 424/200 |
| 3,948,940 | 4/1976 | Drabek | 424/200 |

FOREIGN PATENT DOCUMENTS 1207931 12/1965 Fed. Rep. of Germany.
2248307  4/1973 Fed. Rep. of Germany.
 471155  4/1969 Switzerland.

OTHER PUBLICATIONS

J. of Econ. Ent. 55 (1962) pp. 142–143.

*Primary Examiner*—Allen J. Robinson
*Attorney, Agent, or Firm*—Sprung, Felfe, Horn, Lynch & Kramer

[57] ABSTRACT

N-(O-Ethyl-S-n-propyl-(di)thiophosphoryloxy)-naphthalimides of the formula

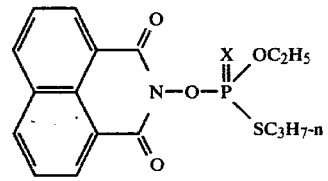

in which
X is oxygen or sulphur, which possess arthropodicidal properties.

7 Claims, No Drawings

COMBATING ARTHROPODS WITH N-(O-ETHYL-S-N-PROPYL-THIOPHOS-PHORYLOXY)-NAPHTHALIMIDES

The present invention relates to and has for its objects the provision of particular new N-(O-ethyl-S-n-propyl-thiophosphoryloxy)-naphthalimides which possess arthropodicidal properties, active composition in the form of mixtures of such compounds with solid and liquid dispersible carrier vehicles, and methods for producing such compounds and for using such compounds in a new way especially for combating pests, e.g. insects, with other and further objects becoming apparent from a study of the within specification and accompanying examples.

It is known that certain N-(O,O-dialkylphosphoryloxy)-naphthalimides, for example N-(O,O-diethyl-phosphoryloxy)-naphthalimide, possess insecticidal properties (see J. Econ. Entomol. 55 (1962), 142–43).

The action of these compounds is however not always satisfactory, especially when low amounts and low concentrations of active compound are used.

The present invention now provides, as new compounds, the N-(O-ethyl-S-n-propyl-(di-)thiophosphoryloxy)-naphthalimides of the general formula

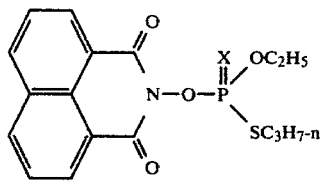

(I)

in which

X represents oxygen or sulphur.

Surprisingly, the N-(O-ethyl-S-n-propyl-(di)-thiophosphoryloxy)-naphthalimides according to the invention exhibit a better activity in combating pests, in particular a better insecticidal action, than the corresponding compounds, known from the prior art, of analogous structure and of the same type of action. The products according to the present invention thus represent a valuable enrichment of the art.

The invention also provides a process for the preparation of an N-(O-ethyl-S-n-propyl-(di)-thiophosphoryloxy)-naphthalimide of the general formula (I), in which an O-ethyl-S-n-propyl-(di)-thiophosphoric acid diester halide of the general formula

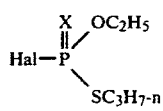

(II), in which

X represents oxygen or sulphur and

Hal represents chlorine or bromine, especially chlorine, is reacted with naphthaloxime, of the formula

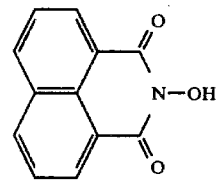

(III), if appropriate in the presence of an acid acceptor and, if appropriate, in the presence of a diluent.

If, for example, O-ethyl-S-n-propyl-dithiophosphoric acid diester chloride and naphthaloxime are used as starting materials, the reaction of these compounds can be outlined by the following equation:

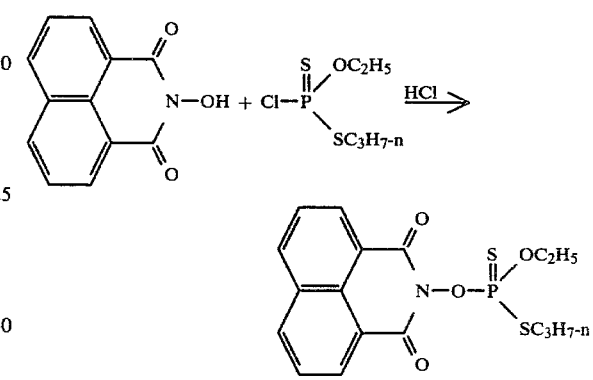

The following may be mentioned as examples of the O-ethyl-S-n-propyl-(di)-thiophosphoric acid diester halides (II) to be used as starting materials: O-ethyl-S-n-propylthiolphosphoric acid diester chloride and O-ethyl-S-n-propyl-dithiophosphoric acid diester chloride. These compounds are already known.

Naphthaloxime (III), to be used as the other starting compound, is also known.

The process for the preparation of the N-(O-ethyl-S-n-propyl-(di)-thiophosphoryloxy)-naphthalimides according to the invention is preferably carried out in the presence of a suitable solvent or diluent. Virtually any of the inert organic solvents can be used for this purpose. These include, as preferences, aliphatic and aromatic, optionally chlorinated, hydrocarbons, such as petrol, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; nitriles, such as acetonitrile and propionitrile; and carboxylic acid amides, such as dimethylformamide.

Any of the customary acid-binding agents can be used as the acid acceptor. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 100° C., preferably at from 10° to 80° C.

The process according to the invention is in general carried out under normal pressure.

To carry out the process according to the invention, the starting materials are usually employed in equimolar amounts. An excess of one or other reactant offers no significant advantages. The reaction is in general carried out in a suitable diluent, in the presence of an acid acceptor, and the reaction mixture is stirred for one or more hours at the required temperature. The reaction mixture is then poured into water and is slightly acidified, if necessary, and the product which has crystallized out is filtered off. The product is characterized by the melting point.

The N-(O-ethyl-S-n-propyl-(di)-thiophosphoryloxy)-naphthalimides according to the invention are distinguished by a very good activity against insects which damage plants. They can therefore be employed successfully as pesticides in plant protection.

Because of their good activity against ectoparasites, the compounds according to the invention can also be used in the veterinary medicine field.

The active compounds are well tolerated by plants, have a favorable level of toxicity to warm-blooded animals, and can be used for combating arthropod pests, especially insects, which are encountered in agriculture, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., Oryzaephilus surinamensis, Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus,* Oscinella frit, Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexaneor paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropririate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects by the application to said animals of a compound according to the present invention, in admixture with a diluent or carrier.

The preparation of the novel compounds is shown in the following illustrative examples:

EXAMPLE 1

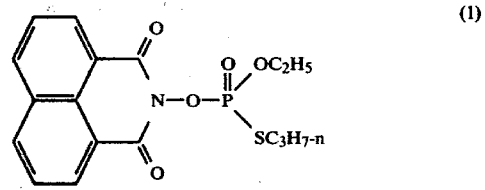

(1)

53.3 g (0.25 mol) of naphthaloxime were dissolved in 200 ml of dimethylformamide and 30 g (0.3 mol) of triethylamine were added. 50.6 g (0.25 mol) of O-ethyl-S-n-propyl-thiolphosphoric acid ester chloride were added dropwise to this mixture at 20° to 30° C. internal temperature. The reaction mixture was stirred for a further hour and was then poured into 1 lit of ice-water. The batch was rendered acid to Congo Red and the product was filtered off, washed until netural and dried. After recrystalli ing the crude product from isopropanol, 57 g (60% of theory) of N-(O-ethyl-S-n-propyl-thiophosphoryloxy)-naphthalimide were obtained. Melting point: 145° C.

EXAMPLE 2

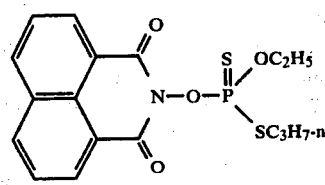
(2)

44 g (0.2 mol) of O-ethyl-S-n-propyl-thiono-thiolphosphoric acid diester chloride were rapidly added dropwise to a solution of 41 g (0.2 mol) of naphthaloxime and 22 g (0.22 mol) of triethylamine in 100 ml of dimethylformamide. In the course thereof, the internal temperature rose from about 25° to 55° C. The reaction mixture was stirred for a further hour and was then poured into water, the batch was stirred thoroughly and the product was filtered off and dried. 75 g (95% of theory) of N-(O-ethyl-S-n-proply-dithiophosphorlyoxy)-naphthalimide were obtained. Melting point: 135° C.

The insecticidal activity of the compounds of this invention is illustrated by the following examples wherein the compounds according to the present invention are each identified by the number (given in brackets) from Example 1 or 2.

EXAMPLE 3

Myzus test

Solvent: 3parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, compound 1 showed a superior activity compared to the prior art.

EXAMPLE 4

Plutella test (long-term action after spraying)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*), which were about 10-15 cm high, were sprayed with the desired preparation of the active compound until dripping wet.

After the specified periods of time the plants were infested with caterpillars of the diamond-back moth (*Plutella maculipennis*). The destruction in % was determined at intervals of 3 days. 100% meant that all the caterpillars had been killed; 0% meant that none of the caterpillars had been killed.

In this test, for example, compound 1 showed a superior activity compared to the prior art.

EXAMPLE 5

Test with parasitic fly larvae

Emulsifier: 80 parts by weight of alkylaryl polyglycol ether

To produce a suitable preparation of active compound, 20 parts by weight of the active compound in question were mixed with the stated amount of the emulsifier and the mixture thus obtained was diluted with water to the desired concentration.

About 20 fly larvae (*Lucilia cuprina*, res.) were introduced into a test tube which contained about 3 ml of a 20% strength suspension of egg yolk powder in water, and which was fitted with a cottonwool plug of appropriate size. 0.5 ml of the active compound preparation was placed on this egg yolk powder suspension. After 24 hours, the degree of destruction was determined.

In this test, for example, compound 1 showed a superior action compared to the prior art.

It will be appreciated that the instant specification and examples are set forth by way of illustration and not limitation, and that various modifications and changes may be made without departing from the spirit and scope of the present invention.

What is claimed is:

1. A N-(O-ethyl-S-n-propyl-thiophosphoryloxy)-naphthalimide of the formula

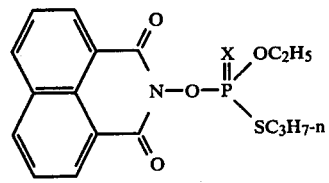

in which
X is oxygen or sulphur.

2. A compound according to claim 1, in which X is sulphur.

3. A compound according to claim 1, in which X is oxygen.

4. An arthropodicidal composition comprising an arthropodicidally effective amount of a compound according to claim 2 in admixture with a diluent.

5. An arthropodicidal composition comprising an arthropodicidally effective amount of a compound according to claim 3 in admixture with a diluent.

6. A method of combating arthropods which comprises applying to the arthropods or to a habitat thereof an arthropodicidally effective amount of a compound according to claim 2.

7. A method of combating arthropods which comprises applying to the arthropods or to a habitat thereof an arthropodicidally effective amount of a compound according to claim 3.

* * * * *